US012642438B1

(12) United States Patent　　(10) Patent No.:　US 12,642,438 B1
Khaleghimeybodi et al.　　　　(45) Date of Patent:　　　Jun. 2, 2026

(54) BLOOD PRESSURE MONITORING VIA IN-EAR DEVICE

(71) Applicant: Meta Platforms Technologies, LLC, Menlo Park, CA (US)

(72) Inventors: Morteza Khaleghimeybodi, Bothell, WA (US); Nils Thomas Fritiof Lunner, Redmond, WA (US); John Rumsfeld, San Francisco, CA (US)

(73) Assignee: Meta Platforms Technologies, LLC, Menlo Park, CA (US)

( * ) Notice: Subject to any disclaimer, the term of this patent is extended or adjusted under 35 U.S.C. 154(b) by 532 days.

(21) Appl. No.: 18/085,928

(22) Filed: Dec. 21, 2022

Related U.S. Application Data

(60) Provisional application No. 63/330,244, filed on Apr. 12, 2022.

(51) Int. Cl.
| | |
|---|---|
| *A61B 5/02* | (2006.01) |
| *A61B 5/00* | (2006.01) |
| *A61B 5/352* | (2021.01) |
| *A61B 7/00* | (2006.01) |
| *H04R 1/10* | (2006.01) |
| *A61B 5/28* | (2021.01) |

(52) U.S. Cl.
CPC ............... *A61B 5/02* (2013.01); *A61B 5/352* (2021.01); *A61B 5/6817* (2013.01); *A61B 5/7278* (2013.01); *A61B 7/00* (2013.01); *H04R 1/1016* (2013.01); *H04R 1/1041* (2013.01); *H04R 1/1075* (2013.01); *A61B 5/28* (2021.01); *A61B 2562/0204* (2013.01)

(58) Field of Classification Search
CPC ......... A61B 5/02; A61B 5/352; A61B 5/6817; A61B 5/7278; A61B 7/00; A61B 5/28; A61B 2562/0204; H04R 1/1016; H04R 1/1041; H04R 1/1075
See application file for complete search history.

(56) References Cited

U.S. PATENT DOCUMENTS

| | | | | |
|---|---|---|---|---|
| 5,853,005 A | * | 12/1998 | Scanlon | ............... A61B 5/6896 381/166 |
| 8,617,082 B2 | | 12/2013 | Zhang et al. | |

(Continued)

OTHER PUBLICATIONS

Liu J., et al., "Multi-Wavelength Photoplethysmography Enabling Continuous Blood Pressure Measurement with Compact Wearable Electronics," IEEE Transactions on Biomedical Engineering, vol. 66, No. 6, Jun. 2019, pp. 1514-1525.

(Continued)

*Primary Examiner* — Catherine M Voorhees
(74) *Attorney, Agent, or Firm* — Greenberg Traurig, LLP

(57) ABSTRACT

An in-ear device (IED) of a wearable system captures audio data from within the ear canal of a user indicative of the user's heartbeat. The IED when worn occludes the user's ear canal, causing amplification of low frequency sounds due to the occlusion effect, and improving the ability of the acoustic sensor to detect the user's heartbeat sounds. The wearable system classifies the audio data to identify portions of the audio data corresponding to a first heart sound and a second heart sound, which correspond to different portions of the heartbeat of the user. The wearable system estimates a blood pressure level of the user based upon the identified heart sounds.

22 Claims, 7 Drawing Sheets

(56)     References Cited

U.S. PATENT DOCUMENTS

| | | | |
|---|---|---|---|
| 9,323,899 B2 * | 4/2016 | Goldstein | ............. G16H 20/10 |
| 10,786,161 B1 * | 9/2020 | Archdeacon | ......... A61B 5/0205 |
| 2012/0095357 A1 * | 4/2012 | Tran | .................... A61B 5/7225 |
| | | | 600/509 |
| 2019/0274655 A1 * | 9/2019 | Thakur | ................... A61B 7/04 |
| 2020/0179706 A1 | 6/2020 | Thakur et al. | |
| 2022/0240802 A1 * | 8/2022 | Khaleghimeybodi | ....................... |
| | | | A61B 5/02416 |
| 2022/0313098 A1 * | 10/2022 | LeBoeuf | ............. A61B 5/7221 |

OTHER PUBLICATIONS

Ma D., et al., "OESense: Employing Occlusion Effect for In-Ear Human Sensing," arXiv:2106.08607v1, Jun. 16, 2021, 13 pages.
Stein S., "Blood Pressure-Sensing Earbuds are Coming in 2020," CNET, Jan. 6, 2020, 3 pages, retrieved from the internet: https://www.cnet.com/health/blood-pressure-sensing-earbuds-are-coming-in-2020/.

* cited by examiner

Front Rigid Body 215

Illuminator 240

Medical Sensor(s) 235

Band 275

Headset 205

Imaging Device 230

Position Sensor 290

Audio Controller 250

Acoustic Sensor 280

Speaker 260

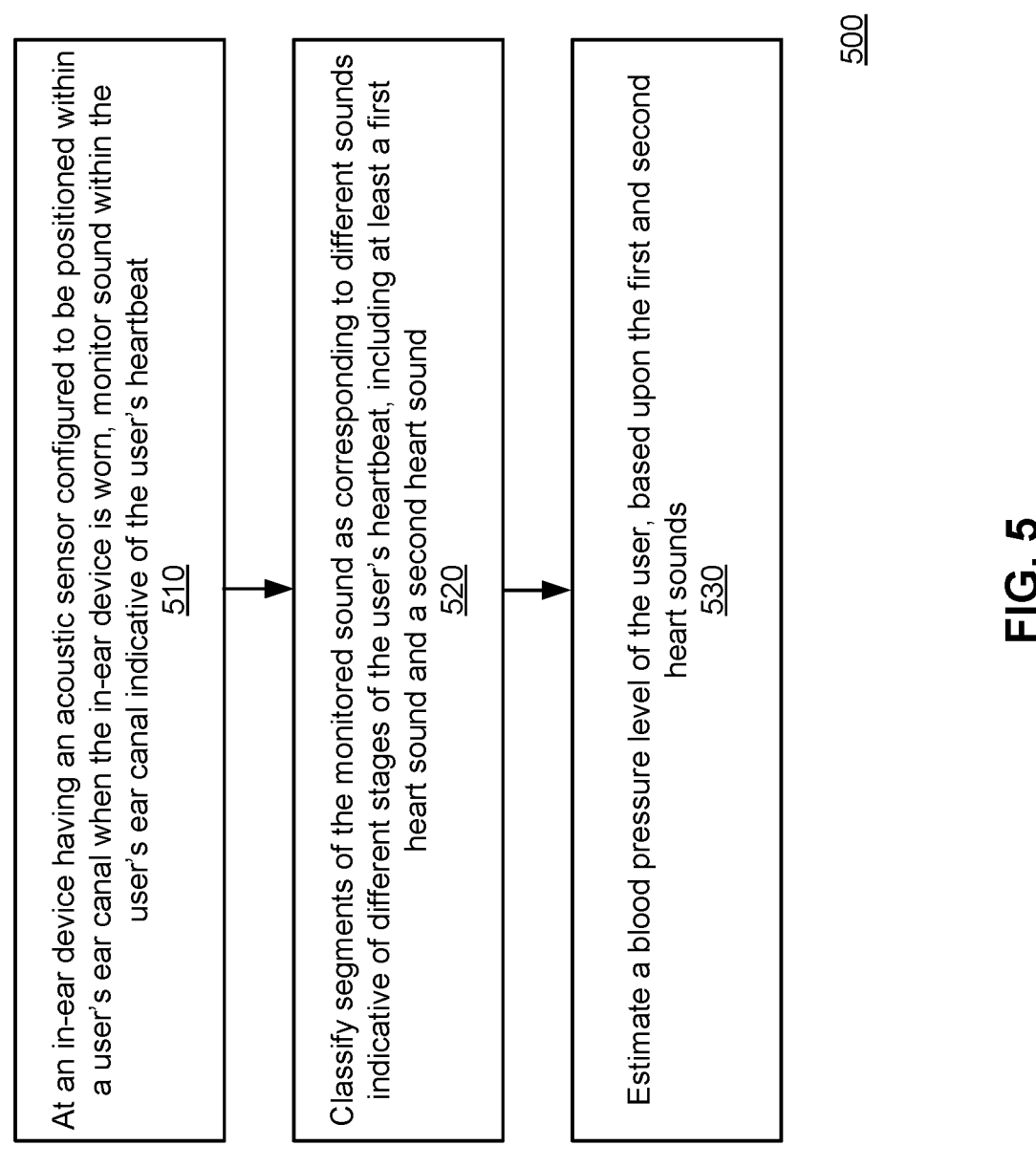

At an in-ear device having an acoustic sensor configured to be positioned within a user's ear canal when the in-ear device is worn, monitor sound within the user's ear canal indicative of the user's heartbeat
510

Classify segments of the monitored sound as corresponding to different sounds indicative of different stages of the user's heartbeat, including at least a first heart sound and a second heart sound
520

Estimate a blood pressure level of the user, based upon the first and second heart sounds
530

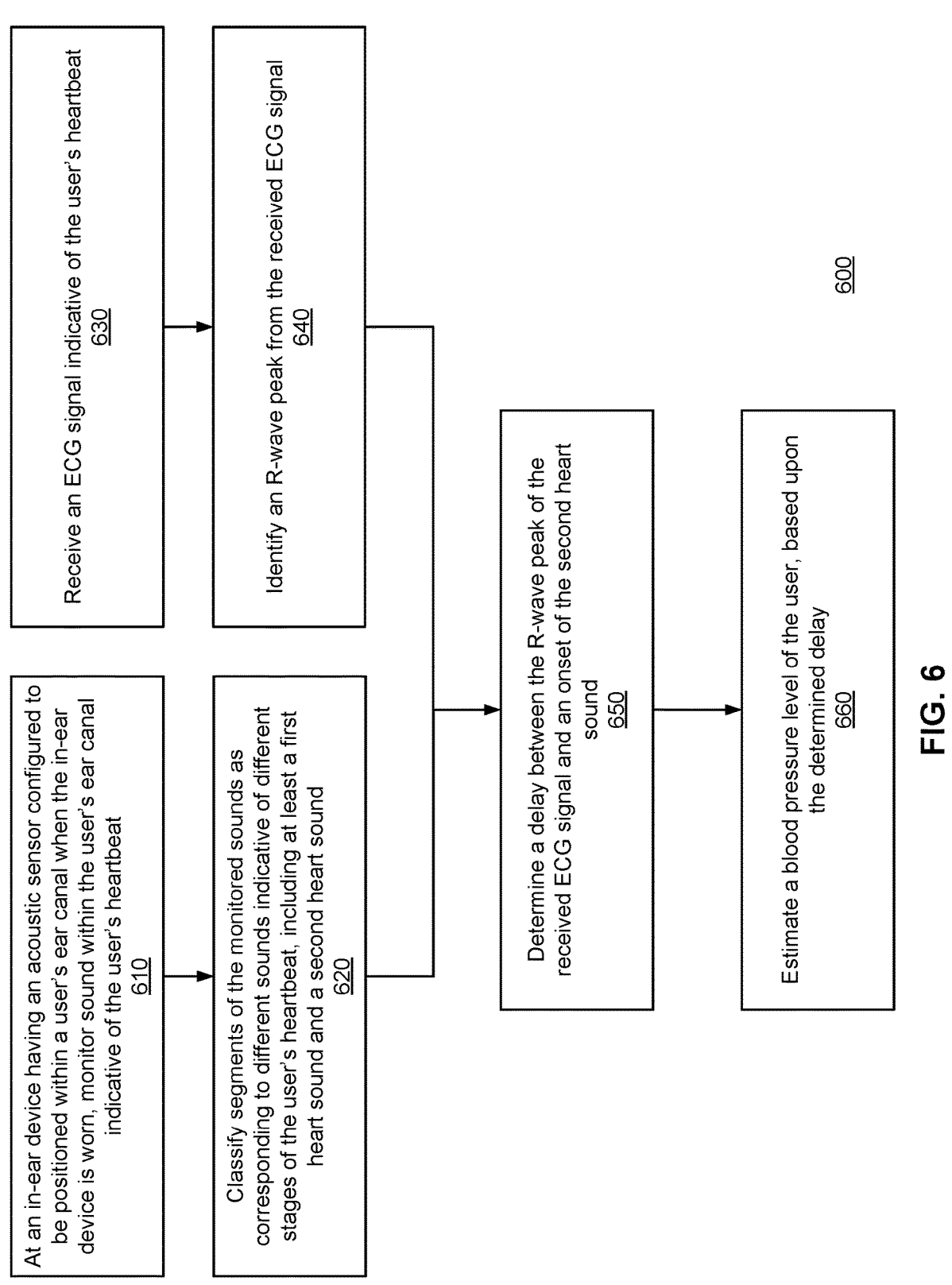

At an in-ear device having an acoustic sensor configured to be positioned within a user's ear canal when the in-ear device is worn, monitor sound within the user's ear canal indicative of the user's heartbeat
610

Classify segments of the monitored sounds as corresponding to different sounds indicative of different stages of the user's heartbeat, including at least a first heart sound and a second heart sound
620

Receive an ECG signal indicative of the user's heartbeat
630

Identify an R-wave peak from the received ECG signal
640

Determine a delay between the R-wave peak of the received ECG signal and an onset of the second heart sound
650

Estimate a blood pressure level of the user, based upon the determined delay
660

BLOOD PRESSURE MONITORING VIA IN-EAR DEVICE

CROSS REFERENCE TO RELATED APPLICATIONS

This application claims a priority and benefit to U.S. Provisional Patent Application Ser. No. 63/330,244, filed Apr. 12, 2022, which is hereby incorporated by reference in its entirety.

FIELD OF THE INVENTION

The present disclosure generally relates to in-ear devices, and specifically relates to blood pressure monitoring via an in-ear device.

BACKGROUND

Heart-rate is a key physiological marker of cardiovascular health and physical fitness. Stethoscopes are typically used by physicians to assess and evaluate the health of cardiac and pulmonary systems, and work by amplifying the created sound inside those organs so the physicians can listen to those body-created sounds and infer if they are operating normally or not. Collecting Phonocardiograms (PCG) using a digital stethoscope allows physicians and scientists to provide data on the timing, relative intensity, frequency, quality, tone, timbre and precise location of the different components of the cardiac sounds. However, PCG collection is generally not performed by a patient using a compact device.

Blood pressure (BP) is another useful metric for evaluating a user's cardiovascular health. Blood pressure is typically measured using cuff based arterial occlusion, in which a cuff is pumped full of air to cut off circulation in the user's artery, and the user's blood pressure is measured as the pressure in the cuff is released. However, such systems are rather bulky and generally lack convenience, and are not suitable for continuous monitoring of the patient's blood pressure over time.

SUMMARY

Embodiments relate to an in-ear device (IED) of a wearable system that can capture audio data from within the ear canal of a user indicative of the user's heartbeat. In some embodiments, the system comprises an in-ear device configured to be placed within an ear canal of a user. The in-ear device includes an acoustic sensor configured to generate an audio signal based upon detected sounds within the ear canal of the user when the in-ear device is worn by the user, wherein the detected sounds are indicative of a heartbeat and breathing rate of the user. The system further comprises a controller configured to estimate blood pressure of the user based in part on the audio signal generated from the detected sounds indicative of the heartbeat of the user.

In some embodiments, the controller is configured to classify portions of the audio signal to identify at least a first heart sound and a second heart sound corresponding to different portions of the heartbeat of the user, and to estimate the blood pressure of the user based in part on the first heart sound and the second heart sound. In some embodiments, the controller is further configured to receive electrocardiogram (ECG) data of the user, and to estimate the blood pressure of the user based on the audio signal and the ECG data.

BRIEF DESCRIPTION OF THE DRAWINGS

FIG. 5 is a flowchart of a method for measuring a blood pressure of a user using acoustic data collected using an in-ear device, in accordance with one or more embodiments.

FIG. 6 is a flowchart of a method for measuring a blood pressure of a user using acoustic data collected using an in-ear device in conjunction with ECG data, in accordance with one or more embodiments.

Figure 1:
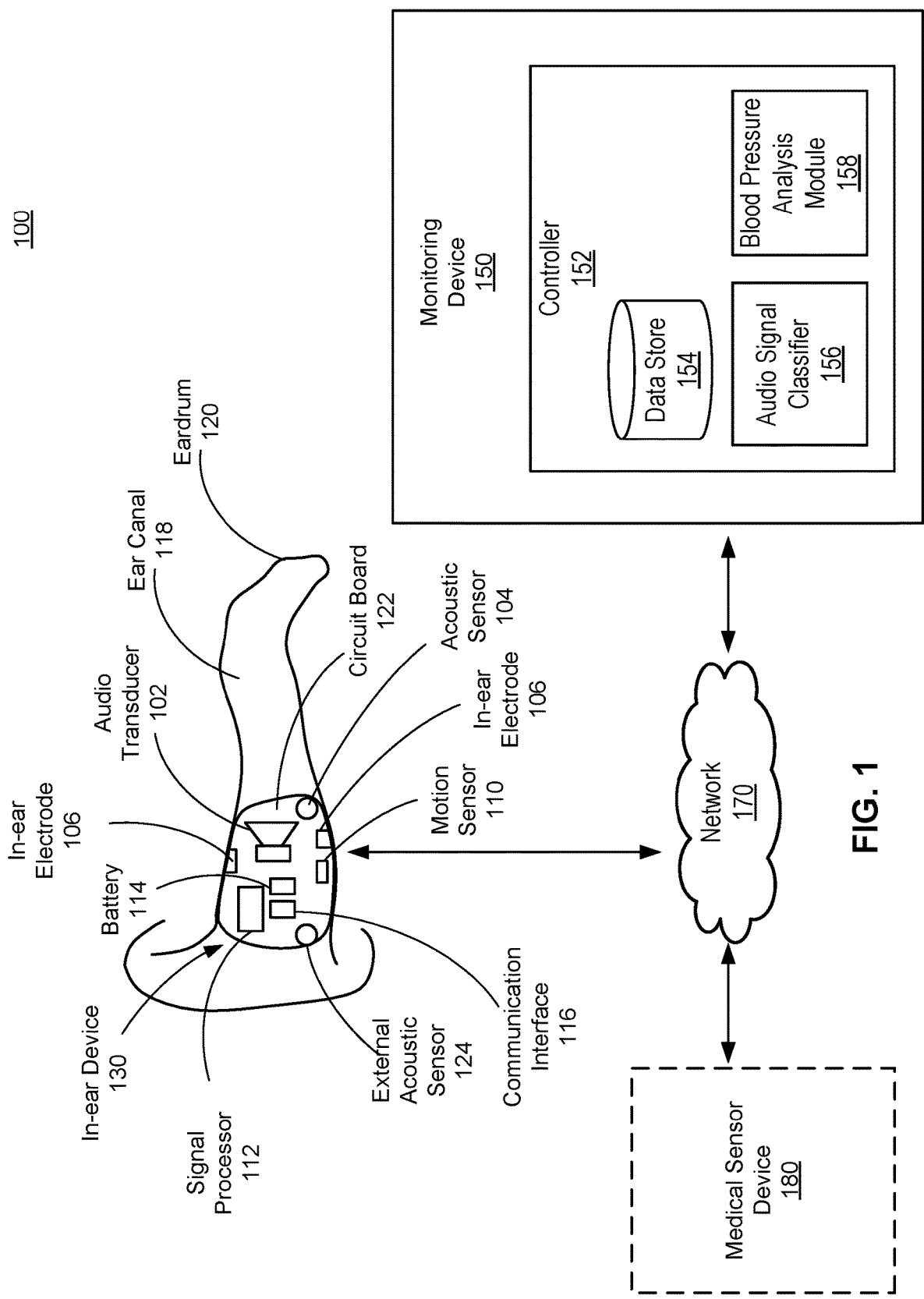
FIG. 1 is a block diagram of a blood pressure monitoring system 100, in accordance with one or more embodiments.

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION

A user's heartbeat produces sounds that travel through the user's body. By measuring and analyzing these sounds (e.g., via a stethoscope or a phonocardiogram (PCG)), the user's heart-rate and other derivative metrics can be inferred, which may be used to monitor the user's cardiovascular health and physical fitness.

Blood pressure is another useful metric for evaluating a user's cardiovascular health. Blood pressure is typically measured using a cuff-based device (e.g., an arm cuff), in which the cuff is pumped full of air to cut off circulation in the user's artery, and the user's blood pressure (e.g., systolic and diastolic pressure) is measured as the pressure in the cuff is released. However, cuff-based blood pressure measurement is not suitable for continuous monitoring of the user's blood pressure over time.

In some embodiments, a system for monitoring a user's blood pressure based on detected sounds indicative of the user's heartbeat is described. The system includes an in-ear device (IED) and a controller. The in-ear device is configured to be placed within an ear canal of a user. The in-ear device includes an inner microphone assembly comprising an in-ear acoustic sensor configured to detect a heartbeat of the user. The controller configured to estimate blood pressure of the user based in part on the detected heartbeat.

In some embodiments, the in-ear acoustic sensor is configured to detect sounds within the user's ear canal that are indicative of the user's heartbeat, and generate an audio signal based on the detected sound. In some embodiments, the IED, when worn, occludes the user's ear canal, facilitating detection of low frequency sounds such as those caused by the user's heartbeat, due to the occlusion effect.

The generated audio signal is processed by the controller (which may be of the IED or of a device provided separately from the IED) to classify portions of the audio signal as corresponding to different heart sounds indicative of different stages of the user's heartbeat. The controller is further configured to analyze properties of the identified heart sounds to estimate a blood pressure level of the user, e.g., based on an intensity ratio of a first heart sound to a second heart sound, a time delay between an onset of the first heart sound and an onset of the second heart sound, spectral content of the second heart sound, or some combination thereof. Using the audio signals generated by the inner microphone assembly of the IED, the user's blood pressure can be monitored over an extended period of time. The user of this IED may choose to share this continuous blood pressure data (or portions of this data) with their trusted medical agencies (e.g., hospitals, clinics, universities) and/or their physicians.

In some embodiments, the collected blood pressure data may be used to generate reports communicated to the user, or shared with the user's physician and/or trusted medical agencies for use in medical advice and consultations. For example, in some embodiments, the controller may be configured to notify the user of their estimated blood pressure level via the IED, or via a display of a separate device. These reports may be communicated periodically, or when the user's estimated blood pressure level reaches a predetermined threshold. In some cases, the controller analyzes the user's measured measure blood pressure values and changes in the user's blood pressure over time, and may identify when changes in the user's blood pressure meets certain conditions. For example, if the controller identifies rapid changes in the user's characterized blood pressure values that exceed a threshold rate, the controller can notify the user of such rapid changes and/or prompt the user to take some type of remedial action (e.g., going to an emergency care, taking their medications, calling their physicians or nurses, etc.).

In some embodiments, the IED may also include additional components such as a plurality of in-ear electrodes, motion sensors, audio transducers, or some combination thereof. Some embodiments of the in-ear device have different components than those described here. Similarly, in some cases, functions can be distributed among the components in a different manner than is described here. In some embodiments, the user's heart sound data may be cross-referenced with other types of collected data (such as ECG data collected using the plurality of in-ear electrodes or via other means) to estimate the user's blood pressure.

Embodiments discussed herein may include or be implemented in conjunction with an artificial reality system. Artificial reality is a form of reality that has been adjusted in some manner before presentation to a user, which may include, e.g., a virtual reality (VR), an augmented reality (AR), a mixed reality (MR), a hybrid reality, or some combination and/or derivatives thereof. Artificial reality content may include completely generated content or generated content combined with captured (e.g., real-world) content. The artificial reality content may include video, audio, haptic feedback, or some combination thereof, any of which may be presented in a single channel or in multiple channels (such as stereo video that produces a three-dimensional effect to the viewer). Additionally, in some embodiments, artificial reality may also be associated with applications, products, accessories, services, or some combination thereof, that are used to create content in an artificial reality and/or are otherwise used in an artificial reality. The artificial reality system that provides the artificial reality content may be implemented on various platforms, including a wearable device (e.g., headset) connected to a host computer system, a standalone wearable device (e.g., headset), an in-ear device, a mobile device or computing system, or any other hardware platform capable of providing artificial reality content to one or more viewers.

FIG. 1 is a block diagram of a blood pressure monitoring system 100, in accordance with one or more embodiments. The blood pressure monitoring 100 may include an in-ear device 130, a monitoring device 150, a medical sensor device 180, and a network 170. The in-ear device 130 fits within an ear canal 118 of a user and captures various types of data from within the ear canal 118. The monitoring device 150 receives the data from the in-ear device 130 via the network 170 and determines health-based measurements of the user (e.g., heart rate, breathing rate, blood pressure, etc.) using the data. Some embodiments of the in-ear device 130 and monitoring device 150 have different components than those described here. Similarly, in some cases, functions can be distributed among the components in a different manner than is described here. For example, some or all of the processing for blood pressure analysis by the monitoring device 150 as described herein may be performed by the in-ear device 130. In some embodiments, some or all the sensors of the in-ear device 130 may also be in the medical sensor device 180. In some embodiments, the medical sensor device 180 may correspond to a hospital-grade device to be used in a hospital or clinic setting for blood pressure monitoring, and where the in-ear device 130 is used to measure blood pressure data in out-of-clinic settings when the medical sensor device 180 is unavailable. In other embodiments, the medical sensor device 180 may correspond to a cuff-based device for blood pressure measurement, and where the in-ear device 130 is used to monitor blood pressure data over time, allowing for the user's blood pressure levels to be monitored when the medical sensor device 180, which can only be used intermittently, is not being used. In some embodiments, the medical sensor device 180 may be used as a ground-truth device to calibrate the monitoring device 150, e.g., calibrate how the monitoring device analyzes data received via the in-ear device 130 to perform continuous blood pressure monitoring.

The in-ear device 130 may include an audio transducer 102, an (in-ear) acoustic sensor 104, in-ear electrodes 106, a motion sensor 110, a signal processor 112, a battery 114, a communication interface 116, and an external acoustic sensor 124. These components of the in-ear device 130 may be mounted to a circuit board 122 that connects the components to each other.

The audio transducer 102 is a speaker that generates sound from audio data and outputs the sound into the ear canal 118. In some embodiments, there may be a plurality of audio transducers 102 (e.g., covering different frequency bands using crossover filters). The audio transducer 102 may be used to provide audio messages to the user. For example, the audio transducer 102 may be used to communicate a blood pressure of the user or notify the user when a blood pressure of the user indicates a potential health problem. The audio transducer 102 may also be used to present other types of audio content to the user, e.g., by broadcasting sound towards the user's eardrum 120. In some embodiments, the audio transducer 102 re-broadcasts sound from the local area detected by the external acoustic sensor 124, such that the in-ear device 130 provides hear-through functionality even though it is occluding the user's ear canal 118. In some embodiments, the audio transducer may play audio content to assist the user in controlling their blood pressure level, e.g., soothing and calming audio contents (e.g., music) that may help the user to calm down and decrease their blood pressure.

The acoustic sensor 104 includes one or more microphones oriented to capture sounds with the ear canal 118 of the user that are caused by a heartbeat of the user, e.g., audio data of sound pressure inside the ear canal 118 caused by the user's tissue movements caused by the user's heartbeat. In some embodiments, the acoustic sensor 104 includes one or more acoustic microphones, vibrometers, accelerometers, contact microphones, other type of sensor that detects acoustic pressure waves, or some combination thereof. For example, the acoustic sensor 104 may comprise a vibrometer configured to capture tissue movements inside the ear canal of the user caused by the user's heartbeat. In some embodiments, the acoustic sensor 104 is a micro-electromechanical systems (MEMS) microphone. The acoustic sensor 104 is configured to detect acoustic pressure waves and convert the detected pressure waves into an electric format (analog or digital).

As sounds caused by the heartbeat may include low frequency components outside the typical range of human hearing, the acoustic sensor 104 may be configured to detect low-frequency sounds, such sounds within the infrasound range, e.g., below 20 Hz. In some embodiments, the acoustic sensor 104 is configured to detect sounds between 5 and 50 Hz. In other embodiments, the acoustic sensor 104 is configured to detect sounds between 5 Hz and 400 Hz. In addition, by placing the in-ear device 130 within the ear canal such that the in-ear device 130 occludes the ear canal, the sealed or occluded ear-canal causes amplification of low frequency sounds due to the occlusion effect. This improves the ability of the acoustic sensor 104 located within the sealed cavity of the ear canal to detect spectral content of sounds within the ear canal caused by the user's heartbeat corresponding to low frequencies, due to this content being amplified by the occlusion effect.

Although FIG. 1 shows a single acoustic sensor 104 within the in-ear device 130, in other embodiments, the in-ear device 130 may include multiple acoustic sensors 104, and/or acoustic sensors of different types. For example, in some embodiments, the acoustic sensor 104 may include a microphone as well as a vibrometer. In some embodiments, where the in-ear device 130 comprises two or more acoustic sensors 104, electrical signals measured by each of the two or more in-ear electrodes may be aggregated (e.g., averaged) to generate an overall acoustic signal measurement. In some embodiments, multiple acoustic sensors 104 may be positioned at different locations one in-ear device 130.

In some embodiments, the in-ear device 130 contains additional components for capturing other biometric data of the user. For example, the in-ear electrodes 106 may capture electrical signals indicating pulses of the user's heartbeat through the user's ear canal 118, representing the biopotentials created by the pulsation of the user's heart. The electrical signals captured by the in-ear electrodes 106 may be used to generate electrocardiogram (ECG) data defining waveform that represents the electrical activity that is taking place within the heart (e.g., alone in combination with electrical signals captured by other electrodes, such as an out-of-ear electrode (not shown)). The in-ear electrodes 104 are positioned at locations on the in-ear device such that they contact a surface of the user's ear canal 118 when the in-ear device 130 is worn by the user. In some embodiments, for better ECG signal quality, the locations of the in-ear electrodes 104 on the in-ear device 130 are selected to contact surfaces of the user's ear canal near the user's arteries when the in-ear device 130 is worn by the user, such as behind the user's tragus. In some embodiments, the in-ear electrodes 104 are dry electrodes that may be directly in contact with the tissue of the user. A dry electrode does not need gel or some other type of medium or layer between the in-ear electrodes and the tissue. The in-ear electrodes 104 may include hard material electrodes (e.g., including gold-plated brass, iridium oxide, etc.) or soft and/or stretchable material electrodes (e.g., including conductive textiles, conductive polymers, carbon allotropes such as graphene or carbon nanotubes, or poly(3,4-ethylenedioxythiophene) polystyrene sulfonate (PEDOT:PSS). In some embodiments where the in-ear device comprises a plurality of in-ear electrodes, electrical signals measured by each of the plurality of in-ear electrodes may be aggregated (e.g., averaged) to generate an overall electrical signal measurement. The plurality of in-ear electrodes may be positioned on the in-ear device to contact different locations in the user's ear or ear canal.

In some embodiments, the in-ear device 130 includes a motion sensor 110 configured to capture motion data of the tissue movements inside the ear canal 118 of the user caused by the user's heartbeat. In some embodiments, the motional sensor 110 may correspond to an accelerometer, vibrometer, contact microphone, or inertial measurement unit (IMU). In some embodiments, the motion sensor 110 may be included as part of the one or more acoustic sensors 104.

The signal processor 112 performs various types of processing to facilitate the capturing of sensor data. For example, in some embodiments, the signal processor 112 includes an analog to digital converter (ADC) that converts the sensor data from the acoustic sensor 104, in-ear electrodes 106, and/or motion sensor 110 into digital data representing waveforms, e.g., convert data from the acoustic sensor 104 into an audio signal waveform. The signal processor 112 may also perform processing of received sensor data (e.g., synchronize data from different sensors in time to facilitate determination of health metrics). The signal processor 112 may also include a digital to analog converter (DAC) that converts digital audio data into analog audio data for rendering by the audio transducer 102. For example, the signal processor 112 may provide audio messages relating the user's health metric data (e.g., data indicating abnormal cardiac events) to the audio transducer 102 for rendering to the user.

The battery 114 provides power to the other components of the in-ear device 130. The battery 114 allows the in-ear device 130 to operate as a mobile device. The battery 114 may be rechargeable via wire or wirelessly.

The communication interface 116 facilitates (e.g., wireless) connection of the in-ear device 130 to other devices, such as the monitoring device 150 via the network 170. For example, the communication interface 116 may transfer data (e.g., audio signal data) generated by the in-ear device 130 to the monitoring device 150 for analysis. The in-ear device 130 may also receive biometric data (e.g., blood pressure level values), audio messages, or other types of information determined from the monitoring device 150 via the communication interface 116 for presentation to the user. In some embodiments, the communication interface 116 includes an antenna and a transceiver.

The medical sensor device 180 is a device that includes one or more sensors used to capture biometric data of the user. The biometric data captured by the medical sensor device 180 may be used in connection with the sensor data collected at the in-ear device 130. The medical sensor device 180 may include an acoustic sensor 104, motion sensor 110, one or more electrodes, an imaging device, or some combination thereof. The medical sensor device 180 may be a headset, a cuff, a smartphone, a wearable device (e.g., bracelet, watch, etc.), or some other device that can be worn near the skin of the user. For example, in some embodiments, the medical sensor device 180 may correspond to a medical- or hospital-grade cuff for blood pressure measurement. In some embodiments, the medical sensor device 180 may be used to supplement data generated using the in-ear device 130, and/or calibrate settings of the in-ear device 130 or monitoring device 150, e.g., based upon comparisons between blood pressure data generated from sensor data captured using the in-ear device 130 and blood pressure data measured using the medical sensor device 180.

The monitoring device 150 may analyze the health metric data (e.g., blood pressure data) of the user based on the data collected by acoustic sensor 104 and/or other sensors of the in-ear device 130 and/or medical sensor device 180. In one embodiment, the monitoring device 150 is a headset or head-mounted display (HMD), as discussed in greater detail below in connection with FIGS. 2A and 2B. Alternatively, the monitoring device 150 may be a device having computer functionality, such as a desktop computer, a laptop computer, a personal digital assistant (PDA), a mobile telephone, a smartphone, a tablet, an Internet of Things (IoT) device, a virtual conferencing device, a cuff, or another suitable device.

The monitoring device 150 includes a controller 152. The controller 152 may include various components that provide functionality for blood pressure estimation and monitoring. The components may include, e.g., one or more processors, a data store 154, an audio signal classifier 156, and a blood pressure analysis module 158. Some embodiments of controller 152 have different components than those described here. Similarly, in some cases, functions can be distributed among the components in a different manner than is described here.

The data store 154 stores data (e.g., audio signal data, monitored blood pressure data, program instruction data corresponding to the various modules of controller 152, and the like) used by the monitoring device 150. The data store 154 may also store data used by the IED 130. The data store 154 (e.g., a non-transitory computer-readable storage medium) and the one or more processors that operate in conjunction to carry out various functions attributed the monitoring device 150 as described herein. For example, the data store 154 may store one or more modules or applications embodied as instructions executable by the one or more processors of the controller 152. The instructions, when executed by the controller 152, cause the controller 152 to carry out the functions attributed to the various modules or applications of the controller 152.

The audio signal classifier 156 analyzes features of the received audio signal data (e.g., corresponding to an audio signal generated by the in-ear acoustic sensor 104) to classify portions of the audio signal data as corresponding to different sounds. In some embodiments, the different sounds classified by the audio signal classifier 156 correspond to heart sounds occurring at different stages of a user's heartbeat. For example, the audio signal classifier module may classify segments of an audio signal corresponding to the user's heartbeat to identify first and second heart sounds S1 and S2. In some embodiments, the audio signal classifier 156 comprises a trained classification model trained to classify segments of the audio signal data as corresponding to the first heart sound S1 or the second heart sound S2.

The first heart sound S1 occurs at the onset of ventricular contraction, during the closure of the mitral and the tricuspid valves, while the second heart sound S2 marks the end of ventricular systole and the beginning of the ventricular relaxation, following the closure of the aortic and pulmonary valves. The onset of second heart sound corresponds to the closure of the aortic valve at the end of ventricular systole when the aortic pressure exceeds ventricular pressure. In some embodiments, the audio signal classifier 156 determines, for each identified heart sound, an onset time of the heart sound, a duration of the heart sound, an intensity of the heart sound, or some combination thereof. In some embodiments, the audio signal classifier 156 may determine, based on the identified heart sounds, a heart rate of the user, e.g., based on a time delay between consecutive occurrences of the same heart sound.

The blood pressure analysis module 158 is configured to receive classified audio data from the audio signal classifier 156, and to determine an estimate of the user's blood pressure. In some embodiments, the classified audio data may include at least portions of the audio signal waveform (e.g., generated by the in-ear acoustic sensor 104 and/or processed by the signal processor 112) determined by the audio signal classifier 156 as corresponding to the first and second heart sounds. In some embodiments, the classified audio data may include data indicating an onset time of one or more heart sounds, a duration of one or more heart sounds, an intensity level of one or more heart sounds, waveform data of one or more heart sounds, or some combination thereof. The blood pressure analysis module 158 analyzes the received classified audio data to determine a blood pressure of the user. In some embodiments, the blood pressure analysis module 158 determines the blood pressure of the user using the classified audio data in conjunction with other sensor data (e.g., ECG data) to determine blood pressure data for the user.

In some embodiments, the blood pressure analysis module 158 uses data from different sensors to determine blood pressure data over time. For example, in some embodiments, the blood pressure analysis module 158 receives classified audio data for determining blood pressure data during a first time period, and blood pressure data measured using the medical sensor device 180 during a second time period. In some embodiments, the blood pressure analysis module 158 may use the blood pressure data measured by the medical sensor device 180 to calibrate the blood pressure data determined using the classified audio data and/or to calibrate the blood pressure estimation algorithms used determine the blood pressure data using the classified audio data, in order to improve the accuracy of how the received classified audio data is mapped to blood pressure level. In some embodiments, the calibration is performed is specific to individual users.

In some embodiments, the blood pressure analysis module 158 analyzes blood pressure data to generate messages and reports. For example, blood pressure data may be analyzed to determine user health status, such as whether the user's blood pressure is indicative of any cardiac abnormalities. In some embodiments, the blood pressure analysis module 158 analyzes blood pressure based on biological differences (e.g., gender, age, weight, and BMI, etc.) between different users. The blood pressure analysis module 158 may monitor the user's blood pressure history over time and generate real-time information regarding blood pressure data and health status.

In some embodiments, the blood pressure analysis module 158 further provides blood pressure data, analysis, and reporting to other devices. For example, an audio message may be provided to the in-ear device 130 for rendering by the audio transducer 102. In another example, the blood pressure data, analysis, and reporting may be provided to a display of the monitoring device 150. In another example, the blood pressure analysis module 158 provides the blood pressure data, analysis, and reporting to a device associated with a physician or other healthcare worker. In some embodiments, blood pressure analysis module 158 allows the user to opt in to share the history of their measured blood pressure data with their physicians.

Some or all components of the monitoring device 150 may be located in the in-ear device 130. Similarly, some or all the functionality of the monitoring device 150 may be performed by the in-ear device. In some embodiments, the monitoring device 150 is a server connected to the in-ear device 130 via a network 170 that includes the Internet.

The network 170 may include any combination of local area and/or wide area networks, using wired and/or wireless communication systems. In one embodiment, the network 170 uses standard communications technologies and/or protocols. For example, the network 110 includes communication links using technologies such as Ethernet, 802.11 (WiFi), worldwide interoperability for microwave access (WiMAX), 3G, 4G, 5G, code division multiple access (CDMA), digital subscriber line (DSL), BLUETOOTH, Near Field Communication (NFC), Universal Serial Bus (USB), or any combination of protocols. In some embodiments, all or some of the communication links of the network 170 may be encrypted using any suitable technique or techniques.

Figure 2A:
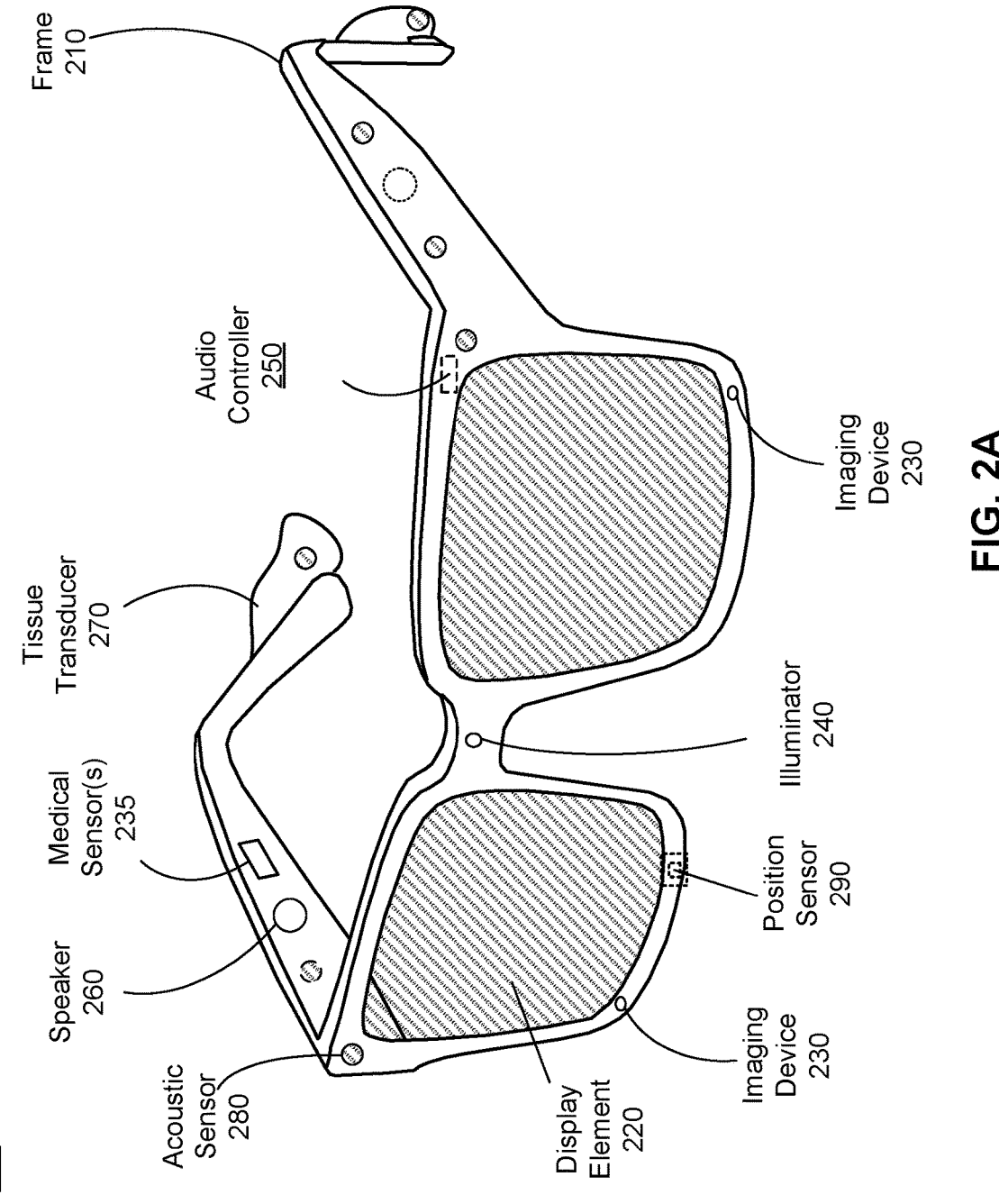
FIG. 2A is a perspective view of a headset implemented as an eyewear device, in accordance with one or more embodiments.

FIG. 2A is a perspective view of a headset 200 implemented as an eyewear device, in accordance with one or more embodiments. The headset 200 is an example of a monitoring device 150. In some embodiments, the headset 200 is an example of a medical sensor device 180. In some embodiments, the eyewear device is a near eye display (NED). In general, the headset 200 may be worn on the face of a user such that content (e.g., media content) is presented using a display assembly and/or an audio system (e.g., including the in-ear device 130). However, the headset 200 may also be used such that media content is presented to a user in a different manner. Examples of media content presented by the headset 200 include one or more images, video, audio, or some combination thereof. The headset 200 includes a frame, and may include, among other components, a display assembly including one or more display elements 220, a depth camera assembly (DCA), an audio system, and a position sensor 190. While FIG. 2A illustrates the components of the headset 200 in example locations on the headset 200, the components may be located elsewhere on the headset 200, on a peripheral device paired with the headset 200 (e.g., in-ear device 130), or some combination thereof. Similarly, there may be more or fewer components on the headset 200 than what is shown in FIG. 2A.

The frame 210 holds the other components of the headset 200. The frame 210 includes a front part that holds the one or more display elements 220 and end pieces (e.g., temples) to attach to a head of the user. The front part of the frame 210 bridges the top of a nose of the user. The length of the end pieces may be adjustable (e.g., adjustable temple length) to fit different users. The end pieces may also include a portion that curls behind the ear of the user (e.g., temple tip, ear piece).

The frame 210 may include one or more medical sensors 235. In some embodiments, the sensors 235 on the headset 200 may replace or supplement one or more components of the in-ear device 130, such as the in-ear electrodes 106 and/or motion sensor 110. For example, in one embodiment, the sensors 235 may include a sensor on the frame 210 at a location near the skin of the user, such as on the temple of the frame 210 or at the user's pinna where the frame 210 rests on the user's ear, having an electrode that contacts the skin of the user that supplements or replaces the in-ear electrode 106. In some embodiments, the sensors 235 may include different sensors from the ones on the in-ear device 130. For example, the in-ear device 130 may include the in-ear electrode 104 while the frame 210 of the headset 205 may include the out-of-ear or world-facing electrode.

The one or more display elements 220 provide light to a user wearing the headset 200. As illustrated the headset includes a display element 220 for each eye of a user. In some embodiments, a display element 220 generates image light that is provided to an eyebox of the headset 200. The eyebox is a location in space that an eye of user occupies while wearing the headset 200. For example, a display element 220 may be a waveguide display. A waveguide display includes a light source (e.g., a two-dimensional source, one or more line sources, one or more point sources, etc.) and one or more waveguides. Light from the light source is in-coupled into the one or more waveguides which outputs the light in a manner such that there is pupil replication in an eyebox of the headset 200. In-coupling and/or outcoupling of light from the one or more waveguides may be done using one or more diffraction gratings. In some embodiments, the waveguide display includes a scanning element (e.g., waveguide, mirror, etc.) that scans light from the light source as it is in-coupled into the one or more waveguides. Note that in some embodiments, one or both of the display elements 220 are opaque and do not transmit light from a local area around the headset 200. The local area is the area surrounding the headset 200. For example, the local area may be a room that a user wearing the headset 200 is inside, or the user wearing the headset 200 may be outside and the local area is an outside area. In this context, the headset 200 generates VR content. Alternatively, in some embodiments, one or both of the display elements 220 are at least partially transparent, such that light from the local area may be combined with light from the one or more display elements to produce AR and/or MR content.

In some embodiments, a display element 220 does not generate image light, and instead is a lens that transmits light from the local area to the eyebox. For example, one or both of the display elements 220 may be a lens without correction (non-prescription) or a prescription lens (e.g., single vision, bifocal and trifocal, or progressive) to help correct for defects in a user's eyesight. In some embodiments, the display element 220 may be polarized and/or tinted to protect the user's eyes from the sun.

In some embodiments, the display element 220 may include an additional optics block (not shown). The optics block may include one or more optical elements (e.g., lens, Fresnel lens, etc.) that direct light from the display element 220 to the eyebox. The optics block may, e.g., correct for aberrations in some or all of the image content, magnify some or all of the image, or some combination thereof.

The DCA determines depth information for a portion of a local area surrounding the headset 200. The DCA includes one or more imaging devices 230 and a DCA controller (not shown in FIG. 2A), and may also include an illuminator 240. In some embodiments, the illuminator 240 illuminates a portion of the local area with light. The light may be, e.g., structured light (e.g., dot pattern, bars, etc.) in the infrared (IR), IR flash for time-of-flight, etc. In some embodiments, the one or more imaging devices 130 capture images of the portion of the local area that include the light from the illuminator 240. As illustrated, FIG. 2A shows a single illuminator 240 and two imaging devices 230. In alternate embodiments, there is no illuminator 240 and at least two imaging devices 230.

The DCA controller computes depth information for the portion of the local area using the captured images and one or more depth determination techniques. The depth determination technique may be, e.g., direct time-of-flight (ToF) depth sensing, indirect ToF depth sensing, structured light, passive stereo analysis, active stereo analysis (uses texture added to the scene by light from the illuminator 240), some other technique to determine depth of a scene, or some combination thereof.

In some embodiments, the imaging devices 230 may also include one or more image devices to capture image data of the user's eye and/or user's head. For example, the imaging devices 230 may capture image data of the user's eye (e.g., for eye tracking purposes), image data of tissue movements of the user's cheek and/or head (e.g., for determination of blood pressure levels).

The audio system provides audio content. The audio system includes a transducer array, a sensor array, and an audio controller 250. However, in other embodiments, the audio system may include different and/or additional components. Similarly, in some cases, functionality described with reference to the components of the audio system can be distributed among the components in a different manner than is described here. For example, some or all of the functions of the controller may be performed by a remote server.

The transducer array presents sound to user. The transducer array includes a plurality of transducers. A transducer may be a speaker 260 or a tissue transducer 270 (e.g., a bone conduction transducer or a cartilage conduction transducer). Although the speakers 260 are shown exterior to the frame 210, the speakers 260 may be enclosed in the frame 210. In some embodiments, instead of individual speakers for each ear, the headset 200 includes a speaker array comprising multiple speakers integrated into the frame 210 to improve directionality of presented audio content. The tissue transducer 270 couples to the head of the user and directly vibrates tissue (e.g., bone or cartilage) of the user to generate sound. The number and/or locations of transducers may be different from what is shown in FIG. 2A. In some embodiments, the transducer is in the in-ear device 130, such as the audio transducer 102. The in-ear device 130 may be a part of the headset 200 or may be separate from the headset 200.

The sensor array detects sounds within the local area of the headset 200. The sensor array includes a plurality of acoustic sensors 280. An acoustic sensor 280 captures sounds emitted from one or more sound sources in the local area (e.g., a room). Each acoustic sensor is configured to detect sound and convert the detected sound into an electronic format (analog or digital). The acoustic sensors 280 may be acoustic wave sensors, microphones, sound transducers, or similar sensors that are suitable for detecting sounds. In some embodiments, the acoustic sensor 124 and the acoustic sensor 108 are substantially the same as the acoustic sensor 280, except that the acoustic sensors 108, 124 are integrated into an IED and the acoustic sensor 280 is integrated into the headset 200.

In some embodiments, one or more acoustic sensors 280 may be placed in an ear canal of each ear (e.g., in the IED 130, acting as binaural microphones). In some embodiments, the acoustic sensors 280 may be placed on an exterior surface of the headset 200, placed on an interior surface of the headset 200, separate from the headset 200 (e.g., part of some other device), or some combination thereof. The number and/or locations of acoustic sensors 280 may be different from what is shown in FIG. 2A. For example, the number of acoustic detection locations may be increased to increase the amount of audio information collected and the sensitivity and/or accuracy of the information. The acoustic detection locations may be oriented such that the microphone is able to detect sounds in a wide range of directions surrounding the user wearing the headset 200. In some embodiments, an acoustic sensor 280 is a component of the in-ear device 130 located outside the ear canal, such as the external acoustic sensor 124.

The audio controller 250 processes information from the sensor array that describes sounds detected by the sensor array. The audio controller 250 may comprise a processor and a computer-readable storage medium. The audio controller 250 may be configured to generate direction of arrival (DOA) estimates, generate acoustic transfer functions (e.g., array transfer functions and/or head-related transfer functions), track the location of sound sources, form beams in the direction of sound sources, classify sound sources, generate sound filters for the speakers 260, or some combination thereof. In some embodiments, the audio controller 250 performs at least a portion of the functionality discussed herein for the controller 152, such as audio signal classification, blood pressure analysis based on audio signal information, and/or generating audio signals (e.g., to report blood pressure information).

The position sensor 290 generates one or more measurement signals in response to motion of the headset 200. The position sensor 290 may be located on a portion of the frame 210 of the headset 200. The position sensor 290 may include an inertial measurement unit (IMU). Examples of position sensor 290 include: one or more accelerometers, one or more gyroscopes, one or more magnetometers, another suitable type of sensor that detects motion, a type of sensor used for error correction of the IMU, or some combination thereof.

In some embodiments, the headset 200 may provide for simultaneous localization and mapping (SLAM) for a position of the headset 200 and updating of a model of the local area. For example, the headset 200 may include a passive camera assembly (PCA) that generates color image data. The PCA may include one or more RGB cameras that capture images of some or all of the local area. In some embodiments, some or all of the imaging devices 230 of the DCA may also function as the PCA. The images captured by the PCA and the depth information determined by the DCA may be used to determine parameters of the local area, generate a model of the local area, update a model of the local area, or some combination thereof. Furthermore, the position sensor 290 tracks the position (e.g., location and pose) of the headset 200 within the room.

Figure 2B:
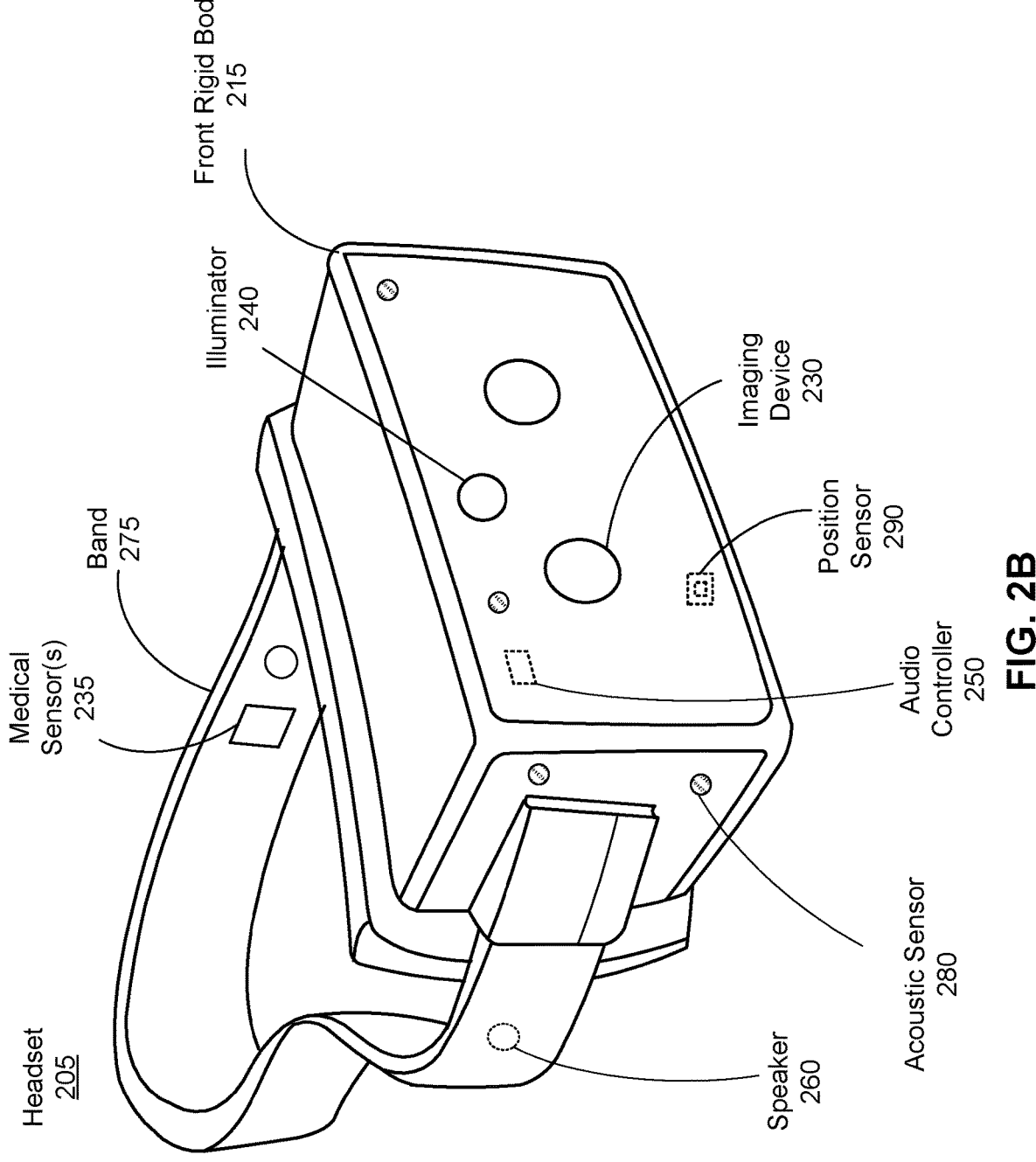
FIG. 2B is a perspective view of a headset implemented as a head-mounted display, in accordance with one or more embodiments.

FIG. 2B is a perspective view of a headset 205 implemented as an HMD, in accordance with one or more embodiments. In embodiments that describe an AR system and/or a MR system, portions of a front side of the HMD are at least partially transparent in the visible band (~380 nm to 750 nm), and portions of the HMD that are between the front side of the HMD and an eye of the user are at least partially transparent (e.g., a partially transparent electronic display). The HMD includes a front rigid body 215 and a band 275. The headset 205 includes many of the same components described above with reference to FIG. 2A, but modified to integrate with the HMD form factor. For example, the HMD includes a display assembly, a DCA, an audio system, a position sensor 290, and one or more medical sensors 235.

FIG. 2B shows the illuminator 240, a plurality of the speakers 260, a plurality of the imaging devices 230, a plurality of acoustic sensors 280, and the position sensor 290. The speakers 260 may be located in various locations, such as coupled to the band 275 (as shown), coupled to front rigid body 215, or may be configured to be inserted within the ear canal of a user (e.g., with in-ear device 130).

Figure 3:
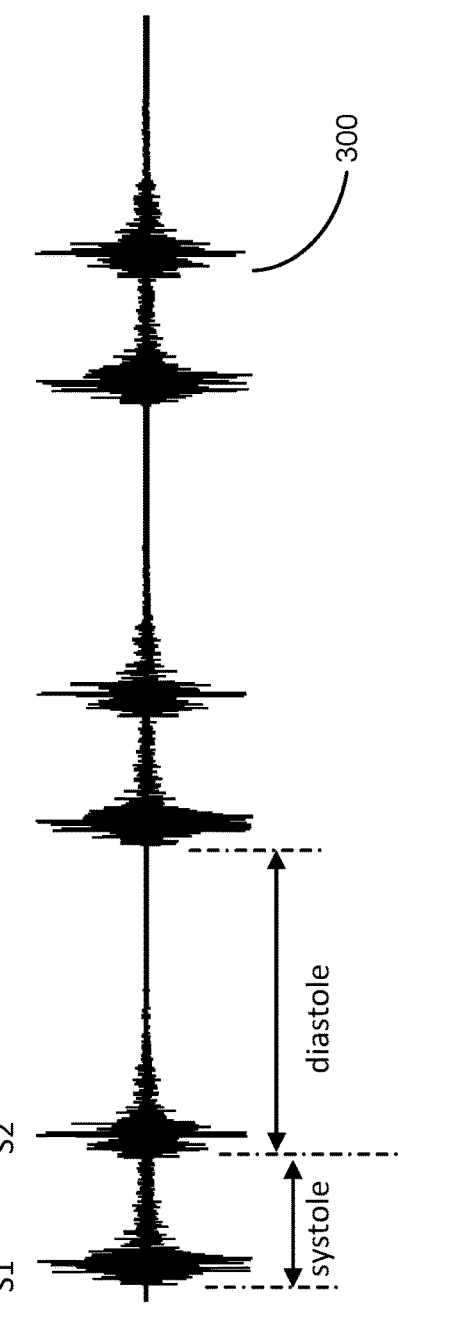
FIG. 3 illustrates an audio signal waveform indicative of a user's heartbeat that may be generated by an audio sensor of an in-ear device, in accordance with some embodiments.

FIG. 3 illustrates an audio signal waveform indicative of a user's heartbeat that may be generated by an audio sensor of an in-ear device, in accordance with some embodiments. In some embodiments, the audio signal 300 shown in FIG. 3 may be generated by the audio sensor 104 positioned within the user's ear canal 118. As shown in FIG. 3, the audio signal 300 contains features corresponding to a plurality of different sounds, indicative of different stages of the user's heartbeat. For example, the first heart sound S1 occurs at the onset of ventricular contraction, during the closure of the mitral and the tricuspid valves, and marks the onset of the systole phase of the user's heartbeat. On the other hand, the second heart sound S2 marks the end of ventricular systole and the beginning of the ventricular relaxation, following the closure of the aortic and pulmonary valves. The onset of second heart sound corresponds to the closure of the aortic valve at the end of ventricular systole when the aortic pressure exceeds ventricular pressure, and corresponds to the onset of the diastole phase of the user's heartbeat.

The controller 152 is configured to estimate blood pressure of the user based in part on the heartbeat detected by the in-ear acoustic sensor (e.g., acoustic sensor 104). The audio signal classifier 156 classifies the audio signal captured by the acoustic sensor 104 by analyzing features of the audio signal and identifying segments of the audio signal as corresponding to different heart sounds, e.g., using a trained classification model. The different heart sounds may include at least a first heart sound S1 and a second heart sound S2.

In some embodiments, the blood pressure analysis module 158 receives audio data from the audio signal classifier 156 corresponding to the first and second heart sounds S1 and S2 (e.g., waveform segments corresponding to each heart sound), and determines an intensity of the created sound pressure of the first and second heart sounds. In some embodiments, the blood pressure analysis module 158 calculates an intensity ratio of the first and second heart sounds (S1/S2). As the intensity ratio S1/S2 has a positive correlation (>90%) with systolic blood pressure (SBP), the blood pressure analysis module 158 is able to estimate the user's SBP using the intensity ratio. In some embodiments, the intensity ratio S1/S2 is calculated based upon a peak intensity of the first and second heart sounds. In other embodiments, the intensity ratio S1/S2 is determined based upon an average intensity of the first and second heart sounds. In other embodiments, the blood pressure analysis module 158 estimates the user's systolic blood pressure based on the overall loudness of the user's heart sounds S1 and S2 instead of the intensity ratio S1/S2.

In some embodiments, the blood pressure analysis module 158 may further determine a time delay corresponding to a delay between an onset of the first heart sound S1 and second heart sound S2. In some embodiments, this time delay information may be used to improve an accuracy of the systolic blood pressure estimation. In some embodiments, the time delay information is determined using digital signal processing algorithms such as cross-correlation algorithms to estimate the delay between S1 and S2, or using onset-to-onset detection to detect the onsets of each heart sound, in order to determine the delay between the heart sounds. In some embodiments, the time delay is estimated using machine learning based algorithms (e.g., deep learning). For example, in some embodiments, the audio signal classifier utilizes a deep neural network to identify the first and second heart sounds from the received audio signal and an onset time of each respective heart sound, from which the blood pressure analysis module 158 is able to determine the time delay.

In some embodiments, the blood pressure analysis module 158 performs spectral analysis on the waveform of the first heart sound S1 or the second heart sound S2. For example, the blood pressure analysis module 158 may perform a Fast Fourier Transform (FFT) or Short-Time Fourier Transform (STFT) on the portion of the audio signal corresponding to the second heart sound S2, to obtain the spectral or frequency content of the second heart sound S2. In some embodiments, the blood pressure analysis module 158, the FFT or STFT is performed on a segment of the audio signal of predetermined length (e.g., 64 msec) containing features of the second heart sound S2. As the spectral contents of the second heart sound S2 is based on the user's systolic blood pressure, the blood pressure analysis module 158 is able to generate an estimate of the user's systolic blood pressure based on the obtained spectral contents of the user's second heart sound S2. For example, in some embodiments, a deep neural network is trained based on ground-truth blood pressure information and frequency contents of the S2 sounds, such that the blood pressure can then be obtained using a regression or classification algorithms. In some embodiments, the spectral contents of the second heart sound S2 are used because the second heart sound S2 typically has greater spectral contents than the first heart sound S1 above 150 Hz.

In some embodiments, the user may wear an in-ear device (e.g., in-ear device 130) in one ear (monaural) or an in-ear device in each ear (binaural). In the case of binaural, acoustic information corresponding to S1 and S2 sounds are simultaneously collected by acoustic sensors from both ears. This enables an additional dataset that can further enhance the accuracy of the classifier and also blood pressure estimation algorithms. For example, in some embodiments, the audio signal classifier may aggregate audio signals collected from each ear when classifying the audio signal to identify the S1 and S2 heart sounds.

While in some embodiments the controller is able to estimate the user's blood pressure level based on only audio signal data as discussed above, in other embodiments, the controller may be configured to estimate blood pressure of the user based on the audio data from the in-ear acoustic sensor 104 in combination with sensor data from other sources, such as ECG data measured using one or more electrodes, e.g., in-ear electrodes 106. As discussed above, in some embodiments, the in-ear electrodes 106 may be used to generate ECG data. In other embodiments, ECG data may be generated using the in-ear electrodes 106 in combination with one or more additional electrodes (e.g., an out-of-ear electrode, not shown), or using a separate device, e.g., a wristband device. In some embodiments, the controller 152 may be configured to estimate the user's blood pressure level using only audio signal data when ECG data is unavailable, and to estimate blood pressure using both audio signal data and ECG data when ECG data is available.

Figure 4:
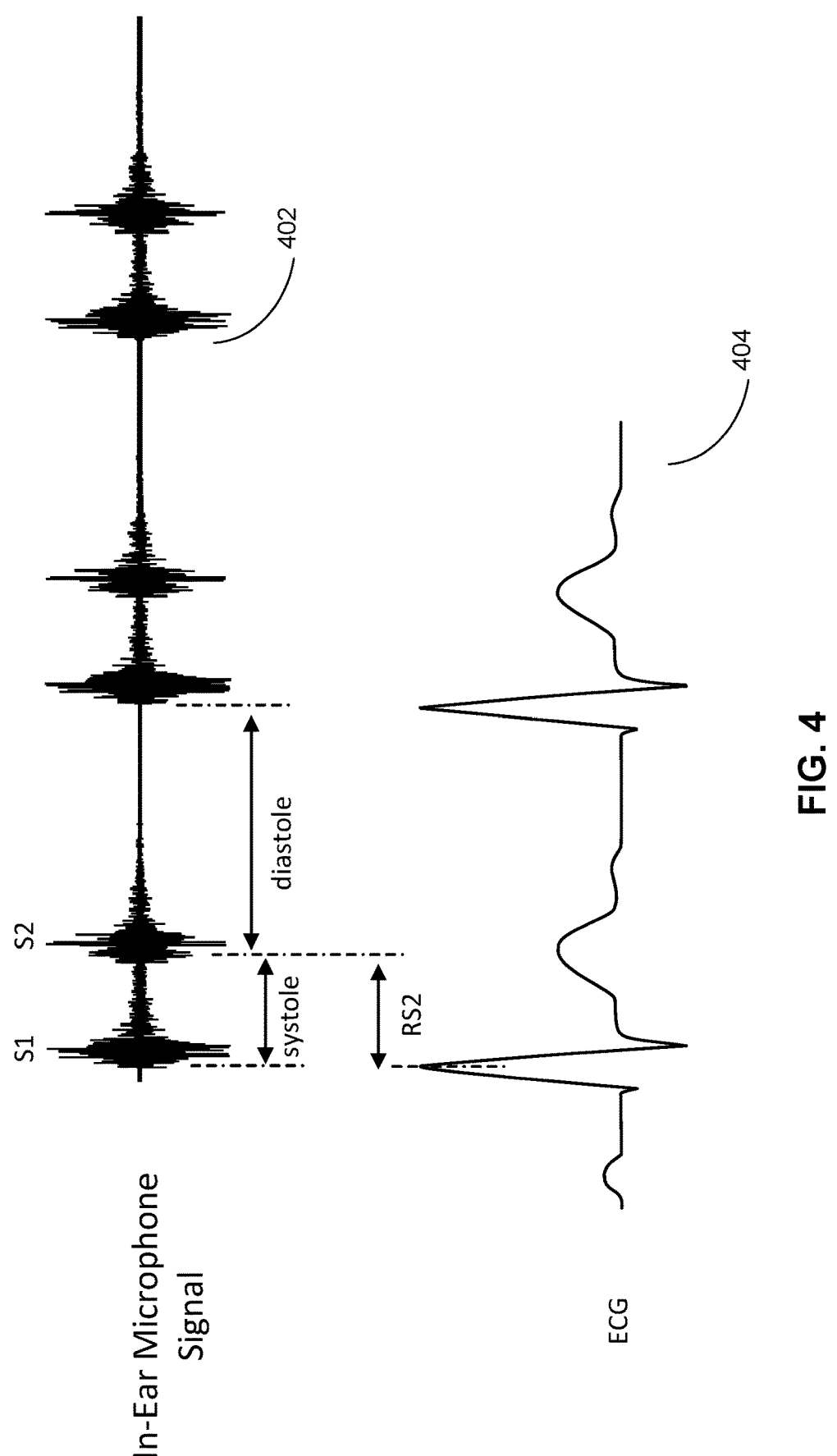
FIG. 4 illustrates the audio signal waveform indicative of a user's heartbeat that may be obtained from an audio sensor of an in-ear device and an ECG waveform of the user, in accordance with some embodiments.

FIG. 4 illustrates the audio signal waveform indicative of a user's heartbeat that may be obtained from an audio sensor of an in-ear device and an ECG waveform of the user, in accordance with some embodiments. The audio signal waveform 402 may correspond to the audio signal waveform 300 illustrated in FIG. 3, and may be generated by the audio sensor 104 positioned within the user's ear canal 118. The ECG waveform 404 may be generated based upon electrical signals generated by the in-ear electrodes 106 (e.g., alone or in combination of signals generated by other electrodes), and/or from some other device (e.g., a wristband device). In some embodiments, the data of the audio signal waveform 402 and the ECG waveform 404 are synchronized in time to facilitate comparison between the different signals. In some embodiments, this synchronization may be performed by the signal processor 112, controller 152, or a combination thereof.

As shown in FIG. 4, the ECG waveform 404 may include pulses corresponding to different stages of the user's heartbeat, including a tallest pulse referred to as an R wave, the peak of which is referred to as the R-peak. The blood pressure analysis module 158 compares data of the ECG waveform 404 and of the audio signal waveform 402 to determine a time delay (shown in FIG. 4 as RS2) between the R-peak of the ECG waveform 404 and the onset of the second heart sound S2 as indicated by the audio signal waveform 402. The magnitude of the time delay RS2 has an inverse relationship with the user's systolic blood pressure. As such, the blood pressure analysis module 158 is able to estimate the user's systolic blood pressure based upon the determined time delay RS2.

In some embodiments, ECG data may also be used in combination with data collected by an optical sensor such as a photoplethysmography (PPG) sensor indicative of tissue movement, to determine a pulse transit time (PTT) that may be used to estimate a user's blood pressure. However, using an audio signal generated by an acoustic sensor in conjunction with ECG may be advantageous because typical MEMS microphones consume less power than typical photoplethysmography (PPG) sensors that are used in combination with the ECG to estimate PTT.

The relationship between the user's blood pressure and their heart sounds may be different for different individual users, and may vary based on factors such as the user's age, height, weight, etc. In order to improve the accuracy of the blood pressure estimates for individual users, in some embodiments, the controller 152 is configured to calibrate its blood pressure estimation algorithms against a ground truth blood pressure measurement for the user, such as a ground truth blood pressure measurement obtained using a cuff-based system. In some embodiments, the ground truth blood pressure measurement is obtained using the medical sensor device 180. In some embodiments, this calibration may be performed periodically. In other embodiments, performance of the calibration may be user-initiated, and the user may receive a notification after a threshold period of time to prompt them to perform a new calibration. In some embodiments, the controller 152 performs calibration by training a deep neural network trained based on ground-truth blood pressure information and information associated with the first and second heart sounds (e.g., intensity ratio S1/S2, time delay between S1 and S2, frequency contents of S2, and/or time delay RS2), such that the blood pressure can then be obtained using based on the information associated with the first and second heart sounds, e.g., via a regression or classification algorithms.

FIG. 5 is a flowchart of a method 500 for measuring a blood pressure of a user using acoustic data collected using an in-ear device, in accordance with one or more embodiments. The process shown in FIG. 5 may be performed by components of a blood pressure monitoring system (e.g., blood pressure monitoring system 100) to monitor the user's blood pressure, the blood pressure monitoring system including an in-ear device (e.g., in-ear device 130) positioned in a user's ear having at least one acoustic sensor positioned within the user's ear canal when the in-ear device is worn by the user. Other entities may perform some or all of the steps in FIG. 5 in other embodiments. Embodiments may include different and/or additional steps, or perform the steps in different orders.

The blood pressure monitoring system, at the in-ear device, monitors 510 sound within the user's ear canal indicative of the user's heartbeat. In some embodiments, the sounds indicative of the user's heartbeat are low frequency sounds that are amplified by the occlusion effect caused by the in-ear device occluding the user's ear canal, facilitating detection by the in-ear acoustic sensor of the in-ear device, which generates an audio signal based upon the detected sound The blood pressure monitoring system classifies 520 segments of the monitored sound as corresponding to different sounds indicative of different stages of the user's heartbeat, including at least a first heart sound and a second heart sound. In some embodiments, the blood pressure monitoring system determines data relating to each classified segment, such as an onset time of the segment, a waveform of the segment, an intensity of the segment, and/or the like.

The blood pressure monitoring system estimates 530 a blood pressure level of the user, based upon the first and second heart sounds. In some embodiments, the blood pressure monitoring system determines an intensity of each of the first and second heart sounds, and estimates the blood pressure level of the user based upon the determined heart sound intensity levels. In some embodiments, the blood pressure monitoring system estimates the blood pressure level based on an intensity ratio of the first and second heart sounds (S1/S2), where the blood pressure level has a positive correlation with the intensity ratio. In some embodiments, the blood pressure level estimation is further modified by a time delay value between an onset of the first heart sound and an onset of the second heart sound. In some embodiments, the blood pressure monitoring system performs spectral analysis on the waveform of the first heart sound S1 and/or the second heart sound S2 (e.g., performing an FFT or STFT on the portion of the audio signal corresponding to the first and/or second heart sound), and estimating the user's blood pressure based on the obtained spectral contents (e.g., based on spectral contents of the second heart sound).

FIG. 6 is a flowchart of a method 600 for measuring a blood pressure of a user using acoustic data collected using an in-ear device in conjunction with ECG data, in accordance with one or more embodiments. The process shown in FIG. 6 may be performed by components of a blood pressure monitoring system (e.g., blood pressure monitoring system 100) to monitor the user's blood pressure, the blood pressure monitoring system including an in-ear device (e.g., in-ear device 130) positioned in a user's ear having at least one acoustic sensor positioned within the user's ear canal when the in-ear device is worn by the user. Other entities may perform some or all of the steps in FIG. 6 in other embodiments. Embodiments may include different and/or additional steps, or perform the steps in different orders.

The blood pressure monitoring system, at the in-ear device, monitors 610 sound within the user's ear canal indicative of the user's heartbeat. The blood pressure monitoring system classifies 620 segments of the monitored sound as corresponding to different sounds indicative of different stages of the user's heartbeat, including at least a first heart sound and a second heart sound. These operations may be similar to that of 510 and 520 described above in relation to FIG. 5.

In parallel with the monitoring of sound within the user's ear canal and the classification of segments of the sound as corresponding to the first heart sound and second heart sound, the blood pressure monitoring system receives 630 an ECG signal indicative of the user's heartbeat. In some embodiments, the ECG signal may be generated based on electrical signals captured by one or more in-ear electrodes on the in-ear device, alone or in combination with one or more additional electrodes, such as an electrode contacting another portion of the user's body. In some embodiments, the controller of the blood pressure monitoring system generates the ECG signal based on electrical signals captured by one or more in-ear electrodes on the in-ear device. In some embodiments, the ECG signal is received from a separate device, e.g., a cuff or wristband device. The blood pressure monitoring system identifies 640 an R-wave peak from the received ECG signal.

The blood pressure monitoring system determines 650 a delay RS2 between the identified R-wave peak of the received ECG signal, and an onset of the second heart sound. In some embodiments, the blood pressure monitoring system includes a signal processor that aligns the waveform of the monitored sound in time with the received ECG signal, to determine the delay between the R-wave peak and the onset of the second heart sound.

The blood pressure monitoring system estimates 660 estimates a blood pressure level of the user based upon the determined time delay. In some embodiments, the blood pressure monitoring system estimates the blood pressure level based upon a known inverse relationship between the time delay RS2 and the user's systolic blood pressure level.

The method 500 and/or 600 may be repeated to continuously monitor blood pressure data of the user over time. In some embodiments, this information may be combined with more intermittent blood measurement measurements, e.g., obtained using medical sensor device 180 and/or other types of blood pressure measurement devices, such as a cuff-based device, to improve an accuracy of the blood pressure estimations and provide a more complete picture of the user's blood pressure levels over time.

In some embodiments, similar techniques may be utilized on other types of wearable devices, such as a wristband device. For example, on a wristband device, a sensitive accelerometer or contact microphone is used to sense pulse-driven tissue vibrations of the user, from which the audio signal classifier may identify the first and second heart sounds. However, because the user's ear is generally a stable location on the user's body, estimating blood pressure based on audio data collected by an in-ear acoustic sensor on the in-ear device may yield a clearer signal with fewer artifacts in comparison to acoustic sensors located on other parts of the user's body. In addition, due to the occlusion effect, the low frequency sounds typically produced by the user's heartbeat are enhanced and more easily captured by the in-ear acoustic sensor. In some embodiments, the in-ear device may be comfortable enough to be worn all-day by the user, allowing the user to monitor their health continuously in an unobtrusive way. This allows the user to measure their blood pressure level in various settings whenever desired.

ADDITIONAL CONFIGURATION INFORMATION

The foregoing description of the embodiments has been presented for illustration; it is not intended to be exhaustive or to limit the patent rights to the precise forms disclosed. Persons skilled in the relevant art can appreciate that many modifications and variations are possible considering the above disclosure.

Some portions of this description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all the steps, operations, or processes described.

Embodiments may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the patent rights. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights, which is set forth in the following claims.

What is claimed is:

1. A system comprising:

an in-ear device configured to be placed within an ear canal of a user, the in-ear device including:

an acoustic sensor configured to generate an audio signal from detected sounds within the ear canal of the user when the in-ear device is worn by the user, wherein the detected sounds are indicative of a heartbeat of the user; and a controller configured to:

classify portions of the audio signal to identify a first heart sound and a second heart sound;

determine a ratio of an acoustic intensity of the first heart sound to an intensity of the second heart sound; and estimate blood pressure of the user by using the acoustic intensity ratio derived from the audio signal as a predictive input to the blood pressure estimation.

2. The system of claim 1, wherein the controller is further configured to:

classify portions of the audio signal to identify at least a first heart sound and a second heart sound corresponding to different portions of the heartbeat of the user; and estimate the blood pressure of the user based in part on the first heart sound and the second heart sound.

3. The system of claim 2, wherein the first heart sound corresponds to an onset of ventricular contraction, and the second heart sound corresponds to an end of ventricular systole and a beginning of ventricular relaxation.

4. The system of claim 2, wherein the acoustic sensor is configured to detect infrasounds.

5. The system of claim 2, wherein the controller is further configured to estimate the blood pressure of the user based upon a time delay between an onset of the first heart sound and an onset of the second heart sound.

6. The system of claim 1, wherein the controller is further configured to:

classify portions of the audio signal to identify at least a first heart sound and a second heart sound corresponding to different portions of the heartbeat of the user;

convert information corresponding to the second heart sound to a frequency domain to obtain spectral content of the second heart sound; and analyze spectral content of the second sound in the frequency domain to estimate the blood pressure of the user.

7. The system of claim 1, wherein the in-ear device is configured to occlude the ear canal of the user.

8. The system of claim 1, wherein the controller is further configure to calibrate estimation of the blood pressure level of the user based upon a received blood pressure level measurement performed by a separate medical device.

9. The system of claim 1, wherein the controller is further configured to:

classify portions of the audio signal to identify at least a first heart sound and a second heart sound corresponding to different portions of the heartbeat of the user;

receive electrocardiogram (ECG) data of the user;

identify, from the received ECG data, an R-wave peak of the ECG data;

determine a time delay between the R-wave peak and an onset of the second heart sound; and estimate the blood pressure of the user based on the determined time delay.

10. The system of claim 9, wherein:

the in-ear device further comprises:

at least one in-ear electrode configured to contact an inner surface of a user's ear when the in-ear device is worn by the user, and wherein the controller is further configured to:

capture electrical signals corresponding to a heartbeat of the user at the at least one in-ear electrode; and generate the ECG data based upon the captured electrical signals.

11. The system of claim 1, wherein at least a portion of the controller is located in the in-ear device.

12. The system of claim 1, wherein the controller is located in a headset.

13. A method comprising:

receiving, from an in-ear device placed within an ear canal of a user, an audio signal based upon sounds detected within the ear canal of the user by an acoustic sensor of the in-ear device, wherein the detected sounds are indicative of a heartbeat of the user;

classifying portions of the audio signal to identify at least a first heart sound and a second heart sound corresponding to different portions of the heartbeat of the user;

determining a ratio of an acoustic intensity of the first heart sound to an intensity of the second heart sound; and estimating blood pressure of the user by using the acoustic intensity ratio derived from the first heart sound or the second heart sound as a predictive input to the blood pressure estimation.

14. The method of claim 13, wherein the first heart sound corresponds to an onset of ventricular contraction, and the second heart sound corresponds to an end of ventricular systole and a beginning of ventricular relaxation.

15. The method of claim 13, wherein the acoustic sensor is configured to detect sound infrasounds.

16. The method of claim 13, wherein estimating blood pressure of the user comprises estimating the blood pressure of the user based upon a time delay between an onset of the first heart sound and an onset of the second heart sound.

17. The method of claim 13, further comprising:

classifying portions of the audio signal to identify at least a first heart sound and a second heart sound corresponding to different portions of the heartbeat of the user;

converting information corresponding to the second heart sound to a frequency domain to obtain spectral content of the second heart sound; and analyzing spectral content of the second sound in the frequency domain to estimate the blood pressure of the user.

18. The method of claim 13, further comprising:

receiving electrocardiogram (ECG) data of the user;

identifying, from the received ECG data, an R-wave peak of the ECG data; and determining a time delay between the R-wave peak and an onset of the second heart sound, wherein estimating the blood pressure of the user based on the determined time delay.

19. A non-transitory computer readable medium having a computer-executable program stored thereon, the program comprising instructions that, when executed by one or more processors of a device, cause the device to:

receive, from an in-ear device placed within an ear canal of a user, an audio signal based upon sounds detected within the ear canal of the user by an acoustic sensor of the in-ear device, wherein the detected sounds are indicative of a heartbeat of the user;

classify portions of the audio signal to identify at least a first heart sound and a second heart sound corresponding to different portions of the heartbeat of the user;

determine a ratio of an intensity of the first heart sound to an acoustic intensity of the second heart sound; and estimate blood pressure of the user by using the acoustic intensity ratio derived from the first heart sound or the second heart sound as a predictive input to the blood pressure estimation.

20. The non-transitory computer readable medium of claim 19, wherein the instructions further cause the device to:

receive electrocardiogram (ECG) data of the user;

identify, from the received ECG data, an R-wave peak of the ECG data;

determine a time delay between the R-wave peak and an onset of the second heart sound; and estimate the blood pressure based on the determined time delay.

21. The system of claim 1, wherein estimating the blood pressure further comprises estimating the blood pressure based on the acoustic intensity ratio of the first and second heart sounds, the blood pressure level having a positive correlation with the acoustic intensity ratio.

22. The method of claim 13, wherein estimating the blood pressure further comprises estimating the blood pressure based on the acoustic intensity ratio of the first and second heart sounds, the blood pressure level having a positive correlation with the acoustic intensity ratio.

\* \* \* \* \*